(12) United States Patent
Kassab

(10) Patent No.: US 7,963,929 B2
(45) Date of Patent: Jun. 21, 2011

(54) DEVICES AND SYSTEMS FOR SIZING OF A GASTRIC POUCH

(75) Inventor: Ghassan S. Kassab, Zionsville, IN (US)

(73) Assignee: DTherapeutics, LLC, Indianapolis, IN (US)

( * ) Notice: Subject to any disclaimer, the term of this patent is extended or adjusted under 35 U.S.C. 154(b) by 344 days.

(21) Appl. No.: 12/211,313

(22) Filed: Sep. 16, 2008

(65) Prior Publication Data

US 2009/0082698 A1    Mar. 26, 2009

Related U.S. Application Data

(60) Provisional application No. 60/974,374, filed on Sep. 21, 2007.

(51) Int. Cl.
| | |
|---|---|
| A61B 5/00 | (2006.01) |
| A61B 5/103 | (2006.01) |
| A61B 5/117 | (2006.01) |
| A61M 29/00 | (2006.01) |

(52) U.S. Cl. ........ 600/593; 600/561; 600/588; 600/590; 604/101.01; 604/101.03; 604/101.05; 604/103; 604/915; 604/919

(58) Field of Classification Search ................ 600/561, 600/587, 588, 590, 593; 604/101.01, 101.03, 604/101.05, 103, 915, 919
See application file for complete search history.

(56) References Cited

U.S. PATENT DOCUMENTS

| | | | | |
|---|---|---|---|---|
| 3,625,793 | A | * | 12/1971 | Sheridan et al. ............... 156/229 |
| 4,091,816 | A | * | 5/1978 | Elam ......................... 128/207.15 |
| 4,315,512 | A | * | 2/1982 | Fogarty ......................... 606/194 |
| 4,402,319 | A | * | 9/1983 | Handa et al. .................. 606/195 |
| 4,423,725 | A | * | 1/1984 | Baran et al. ............. 128/207.15 |
| 4,502,490 | A | * | 3/1985 | Evans et al. .................... 600/593 |
| 4,600,015 | A | * | 7/1986 | Evans et al. .................... 600/593 |
| 4,676,228 | A | * | 6/1987 | Krasner et al. ................ 600/116 |
| 4,693,704 | A | * | 9/1987 | Ogita ............................ 604/515 |
| 4,981,470 | A | * | 1/1991 | Bombeck, IV ............... 600/350 |
| 5,090,957 | A | * | 2/1992 | Moutafis et al. ................ 600/18 |
| 5,186,172 | A | * | 2/1993 | Fiddian-Green ............. 600/353 |
| 5,263,485 | A | * | 11/1993 | Hickey ......................... 600/486 |
| 5,290,306 | A | * | 3/1994 | Trotta et al. ................... 606/194 |
| 5,397,308 | A | * | 3/1995 | Ellis et al. .................. 604/100.3 |
| 5,398,692 | A | * | 3/1995 | Hickey ......................... 600/486 |
| 5,433,216 | A | * | 7/1995 | Sugrue et al. ................. 600/591 |

(Continued)

OTHER PUBLICATIONS

Markus K. Muller, M,; Stefan Wildi, MD, Thomas Scholz, MD, Pierre-Alain Clavien, MD, PhD, and Markus Weber, MD, Laparoscopic Pouch Resizing and Redo of Gastro-jejunal Anastomosis for Pouch Dilatation following Gastric Bypass, Obesity Surgery, 2005, pp. 1089-1095, vol. 15, FD-Communications Inc.

(Continued)

*Primary Examiner* — Max Hindenburg
*Assistant Examiner* — Sean P Dougherty
(74) *Attorney, Agent, or Firm* — Ice Miller LLP

(57) ABSTRACT

Devices, methods, and systems for measuring the size of gastric pouches. At least some embodiments include a catheter comprising an outer elongate tube, an inner elongate tube disposed within the outer elongate tube, a proximal balloon attached to the outer elongate tube, a distal balloon having a first end attached to the outer elongate tube and a second end attached to the inner elongate tube, at least two detection electrodes positioned on the outer elongate tube relative to at least two excitation electrodes, and a pressure transducer positioned on the outer elongate tube.

17 Claims, 7 Drawing Sheets

U.S. PATENT DOCUMENTS

| | | | |
|---|---|---|---|
| 5,514,073 A * | 5/1996 | Miyata et al. | 600/18 |
| 5,695,468 A * | 12/1997 | Lafontaine et al. | 604/96.1 |
| 5,971,955 A * | 10/1999 | Nap et al. | 604/101.5 |
| 6,575,932 B1 * | 6/2003 | O'Brien et al. | 604/101.01 |
| 6,723,053 B2 * | 4/2004 | Ackerman et al. | 600/486 |
| 6,773,452 B2 * | 8/2004 | Shaker | 600/587 |
| 7,454,244 B2 * | 11/2008 | Kassab et al. | 600/547 |
| 7,641,633 B2 * | 1/2010 | Laufer et al. | 604/114 |
| 2002/0010418 A1 * | 1/2002 | Lary et al. | 604/101.4 |
| 2003/0032851 A1 * | 2/2003 | Apple et al. | 600/3 |
| 2004/0015150 A1 * | 1/2004 | Zadno-Azizi | 604/523 |
| 2006/0200075 A1 * | 9/2006 | Zadno-Azizi | 604/101.5 |
| 2006/0212022 A1 * | 9/2006 | Gellman | 604/509 |
| 2008/0077043 A1 * | 3/2008 | Malbrain et al. | 600/547 |
| 2008/0275368 A1 * | 11/2008 | Gregersen et al. | 600/593 |
| 2010/0113939 A1 * | 5/2010 | Mashimo et al. | 600/470 |

OTHER PUBLICATIONS

John D. Halverson, M.D. and Robert E. Koehler, M.D., Gastric bypass: Analysis of weight loss and factors determining success, Surgery, Sep. 1981, pp. 446-455, vol. 90, No. 3, The C.V. Mosby Co.

Peter Forsell, MD, Pouch Volume, Stoma Diameter and Weight Loss in Swedish Adjustable Gastric Banding (SAGB), Obesity Surgery, 1996, pp. 468-473, vol. 6, Rapid Science Publishers, 468-473.

Latham Flanagan, Jr, MD, FACS, Measurement of Functional Pouch Volume following the Gastric Bypass Procedure Obesity Surgery, 1996, pp. 38-43, vol. 6, Rapid Science Publishers.

K. Roberts, A. Duffy, J. Kaufman, M. Burrell, J. Dziura, and R. Bell, Size matters: gastric pouch size correlates with weight loss after laparoscopic Roux-en-Y gastric bypass, Surg. Endosc., 2007, pp. 1397-1402, vol. 21, Springer Science+Business Media.

* cited by examiner

DEVICES AND SYSTEMS FOR SIZING OF A GASTRIC POUCH

PRIORITY

This U.S. Patent Application is related to and claims the benefit of U.S. Provisional Patent Application Ser. No. 60/974,374, entitled "DEVICES, METHODS, AND SYSTEMS FOR SIZING OF A GASTRIC POUCH," filed Sep. 21, 2007, the contents of which is incorporated herein by reference.

BACKGROUND

In order to treat obesity, conventional surgical procedures involve attempts to either (1) restrict food intake into the body via a restrictive bariatric procedure or (2) divert the peristalsis of a person's normal food intake past the small intestine to decrease caloric absorption via a malabsorptive bariatric procedure. There also exists combined procedures in which both of the aforementioned techniques are employed jointly.

Restrictive procedures have encountered more success than malabsorptive ones, with the latter resulting in severe nutritional deficiencies in some cases. In restrictive procedures, the goal is to construct a passageway from the upper portion of the stomach to the lower portion, thereby preventing the stomach from storing large amounts of food and slowing the passage of food from the esophagus to the small intestine. Such a surgery results in the formation of a small pouch on the superior portion of the stomach near the gastroesophageal junction. In the beginning, the formed pouch holds approximately one ounce of food, but later distends to store two to three ounces. The lower outlet of the pouch is approximately one-half inch in diameter or smaller. The pouch diverts the passage of food to the lower portion of the stomach, thus avoiding storage of food in the stomach itself. When the pouch is full, it stimulates a feeling of satiation as well.

Purely restrictive operations for obesity include adjustable gastric banding (AGB) and vertical banded gastroplasty (VBG). These processes do not affect the digestive process. In AGB, a hollow silicone rubber band is placed around the stomach near its upper end, creating a small pouch and a narrow passageway into the rest of the stomach. The band is then inflated with a saline solution through a tube that connects the band to an access port located subcutaneously. It can be tightened or loosened over time to modify the size of the passage by increasing or decreasing the quantity of saline solution. Similarly, VBG utilizes rubber bands but also uses staples to create a small stomach pouch. The procedure involves puncturing the stomach to create a pouch that is not subject to the manual regulation observed in AGB.

In a malabsorptive bariatric procedure, an intestinal bypass is performed resulting in the exclusion of almost all of the small intestine from the digestive tract so that the patient absorbs a smaller amount of calories and nutrients. An example of a malabsorptive procedure is biliopancreatic diversion (BPD), in which about three-fourths of the stomach is removed in order to restrict food intake and decrease stomach acid production. The effect of this procedure is to alter the anatomy of the small intestine via the formation of an alimentary limb that diverts the passage of food past the first portion of the small intestine, including the duodenum and jejunum, and thereby prevents some of the bile and pancreatic juices from digesting some of the ingested food.

Combined operations are the most common bariatric procedures performed today. They restrict both food intake and the amount of calories and nutrients the body absorbs. An example of a combined procedure is the Extended (Distal) Roux-en-Y Gastric Bypass in which a stapling creates a small (15 to 20 cc) stomach pouch completely separated from the remainder of the stomach. The remainder of the stomach is not removed. The outlet from this newly formed pouch empties directly into the lower portion of the jejunum, which decreases caloric absorption. This connection is made by dividing the small intestine just below the duodenum and attaching the lower portion of the jejunum to the newly formed stomach pouch. The other end is connected into the side of the Roux limb of the intestine creating the "Y" shape that gives the technique its name.

There is ample evidence that gastric pouch size is a key factor influencing weight loss after bariatric surgery. There have been reports of an inverse relation between pouch size and excess weight loss; in other words, a smaller pouch will lead to greater weight loss. There is a limit to the minimum dimension, however, for health and safety reasons. Efforts to standardize small pouch size for all patients are important to the success of surgical therapy for morbid obesity.

The size of the pouch is important to the outcome of the procedure for AGB, VBG, or Roux-en-Y. Indeed, the AGB patients require a weekly visit to adjust the size of the pouch for maximum efficacy. Generally, there has been an inability to measure accurately and reproducibly the size of the gastric pouch, although a number of attempts have been made. Some researchers have used intraoperative measurement of pouch size with injected saline through a nasogastric tube before stapling of the stomach. Balloon catheters attached to a nasogastric tube and inflated with fluid have also been used. Nevertheless, the vast majority of bariatric surgeons currently estimate the pouch size using a visual estimate (i.e., transecting the stomach a specific distance for the gastroesophageal junction or between the second and third branches of the left gastric arterial cascade). Postoperatively, radiographic methods have been employed to approximate a three-dimensional pouch size volume from a two-dimensional filled contrast pouch.

The most commonly used method for studying the size and distensibility of hollow organs includes a balloon mounted on a catheter with impedance electrodes for measurement of the cross-sectional area in the middle of the balloon along with the balloon pressure (referred to as impedance planimetry). The distensibility of the organ is derived from computation of parameters such as tension, strain, cross-sectional area distensibility, and compliance ($\Delta CSA/\Delta P$) where $\Delta CSA$ denotes the change in cross-sectional area and $\Delta P$ denotes the change in pressure. Tension is computed using Laplace's law in the form $T=\Delta P^*r$ where $\Delta P$ and r are the transmural pressure and the luminal radius of the organ, respectively.

BRIEF SUMMARY

Various embodiments of devices, methods, and systems for measuring the size of a gastric pouch are disclosed herein. At least some embodiments include a catheter comprising an outer elongate tube having a proximal end and a distal end, an inner elongate tube having a proximal end and a distal end, the inner elongate tube positioned at least partially within the outer elongate tube such that the inner elongate tube is capable of sliding within the outer elongate tube, a proximal balloon surrounding at least a portion of the outer elongate tube near the distal end of the outer elongate tube, the proximal balloon having a first end attached to the outer elongate tube and a second end attached to the outer elongate tube, a distal balloon surrounding a portion of the outer elongate tube distal to the proximal balloon, the distal balloon having a first end attached to the outer elongate tube and a second end attached to the inner elongate tube, at least two excitation electrodes attached to the portion of the outer elongate tube surrounded by the distal balloon, the at least two excitation electrodes capable of attachment to a power source, at least two detection electrodes attached to the outer elongate tube relative to the at least two excitation electrodes, the at least two detection electrodes capable of attachment to a processor, a first pressure transducer attached to the portion of the outer elongate tube surrounded by the proximal balloon, and a second pressure transducer attached to the portion of the outer elongate tube surrounded by the distal balloon. Such embodiments may include three, four, or five or more detection electrodes. Certain embodiments further comprise a first fluid passageway for injecting fluid into the proximal balloon and a second fluid passageway for injecting fluid into the distal balloon.

At least some embodiments include an inner elongate tube comprising at least one gradation at or near the proximal end of the inner elongate tube. Many of such embodiments include at least two gradations positioned on the inner elongate tube a predetermined distance apart. In some embodiments, the gradations comprise notches on the inner elongate tube and the outer elongate tube has a latch at or near the proximal end of the outer elongate tube, the latch being configured to engage one or more of the notches such that the inner elongate tube and the outer elongate tube are reversibly fastened.

In some embodiments, the outer elongate tube comprises a flexible portion near the distal end of the outer elongate tube, the flexible portion capable of being bent into a curve, and the inner elongate tube is flexible such that the inner elongate tube is capable of sliding within the flexible portion of the outer elongate tube when the flexible portion is bent into a curve. In other embodiments, the outer elongate tube comprises a curved portion near the distal end of the outer elongate tube, and the inner elongate tube is flexible such that the inner elongate tube is capable of sliding within the curved portion of the outer elongate tube.

Certain embodiments disclosed herein include a system for measuring the size of a gastric pouch, comprising a catheter having an outer elongate tube, an inner elongate tube positioned at least partially within the outer elongate tube, a proximal balloon attached to the outer elongate tube, a distal balloon having a first end attached to the outer elongate tube and a second end attached to the inner elongate tube, at least two detection electrodes positioned on the outer elongate tube relative to at least two excitation electrodes, and a pressure transducer positioned on the outer elongate tube, a first processor operatively connected to the at least two detection electrodes, the first processor being capable of collecting conductance data and determining a size variable, and a power source operatively connected to the at least two excitation electrodes, wherein the power source is capable of providing current to the excitation electrodes. In at least some embodiments, the catheter further comprises a first fluid passageway for injecting fluid into the proximal balloon and a second fluid passageway for injecting fluid into the distal balloon. In some embodiments, the first processor is operatively connected to the pressure transducer, the first processor being capable of collecting pressure data. However, in other embodiments, there is a second processor operatively connected to the pressure transducer, the second processor being capable of collecting pressure data. In certain embodiments, the size variable comprises an approximate cross-sectional area of the gastric pouch. In others, the size variable comprises an approximate volume of the gastric pouch.

In some embodiments, the system further comprises a fluid source operatively connected to the catheter, such that a fluid from the fluid source can be injected into the proximal balloon or the distal balloon. In certain of those embodiments, the fluid source comprises a syringe.

The system may also further comprise a graphical display screen for displaying pressure data or size variables.

Other embodiments include a method for measuring the size of a gastric pouch, the method comprising the steps of introducing a catheter into an esophagus, the catheter comprising an outer elongate tube, an inner elongate tube disposed within the outer elongate tube, a proximal balloon attached to the outer elongate tube, a distal balloon having a first end attached to the outer elongate tube and a second end attached to the inner elongate tube, at least two detection electrodes positioned on the outer elongate tube between at least two excitation electrodes, and a pressure transducer positioned on the outer elongate tube; locating the gastroesophageal junction using the proximal balloon; adjusting the distal balloon axially to a desired balloon length; injecting a fluid into the distal balloon to extend the distal balloon circumferentially; and determining a size variable of the gastric pouch. In certain embodiments, the step of locating the gastroesophageal junction using the proximal balloon comprises the steps of positioning the proximal balloon at a location at or near the gastroesophageal junction, injecting fluid into the proximal balloon to extend the proximal balloon circumferentially, and measuring a pressure inside the proximal balloon. The step of adjusting the distal balloon axially to a desired balloon length may comprise the step of extending the distal balloon axially by sliding the inner elongate tube within the outer elongate tube. The step of adjusting the distal balloon axially to a desired balloon length may further comprise the step of sliding the inner elongate tube within the outer elongate tube until a gradation on the inner elongate tube is aligned with the proximal end of the outer elongate tube. In some embodiments, the step of adjusting the distal balloon axially to a desired balloon length further comprises the step of sliding the inner elongate tube within the outer elongate tube until a gradation on the inner elongate tube is engaged by a latch on the proximal end of the outer elongate tube, such that the inner elongate tube and the outer elongate tube are reversibly fastened.

The step of adjusting the distal balloon axially to a desired balloon length may comprise the step of shortening the distal balloon axially by sliding the inner elongate tube within the outer elongate tube. The step of adjusting the distal balloon axially to a desired balloon length may further comprises the step of sliding the inner elongate tube within the outer elongate tube until a gradation on the inner elongate tube is aligned with the proximal end of the outer elongate tube. In some embodiments, the step of adjusting the distal balloon axially to a desired balloon length further comprises the step of sliding the inner elongate tube within the outer elongate tube until a gradation on the inner elongate tube is engaged by a latch on the proximal end of the outer elongate tube, such that the inner elongate tube and the outer elongate tube are reversibly fastened.

In certain embodiments, the fluid injected into the distal balloon comprises saline solution.

The step of determining a size variable of the gastric pouch may comprise the step of determining a pressure inside the distal balloon. In addition, the step of determining a size variable of the gastric pouch may comprise the step of determining a cross-sectional area of a portion of the distal balloon. The step of determining a size variable of the gastric pouch may further comprise the step of determining a volume of the distal balloon. The step of determining a size variable of the gastric pouch may comprise the step of determining an approximate length of the gastric pouch.

BRIEF DESCRIPTIONS OF THE DRAWINGS

DETAILED DESCRIPTION

Various embodiments of devices, methods, and systems for measuring the size of a gastric pouch are disclosed herein. It will be appreciated by those of skill in the art that the following detailed description of the disclosed embodiments is merely exemplary in nature and is not intended to limit the scope of the appended claims.

Figure 1:
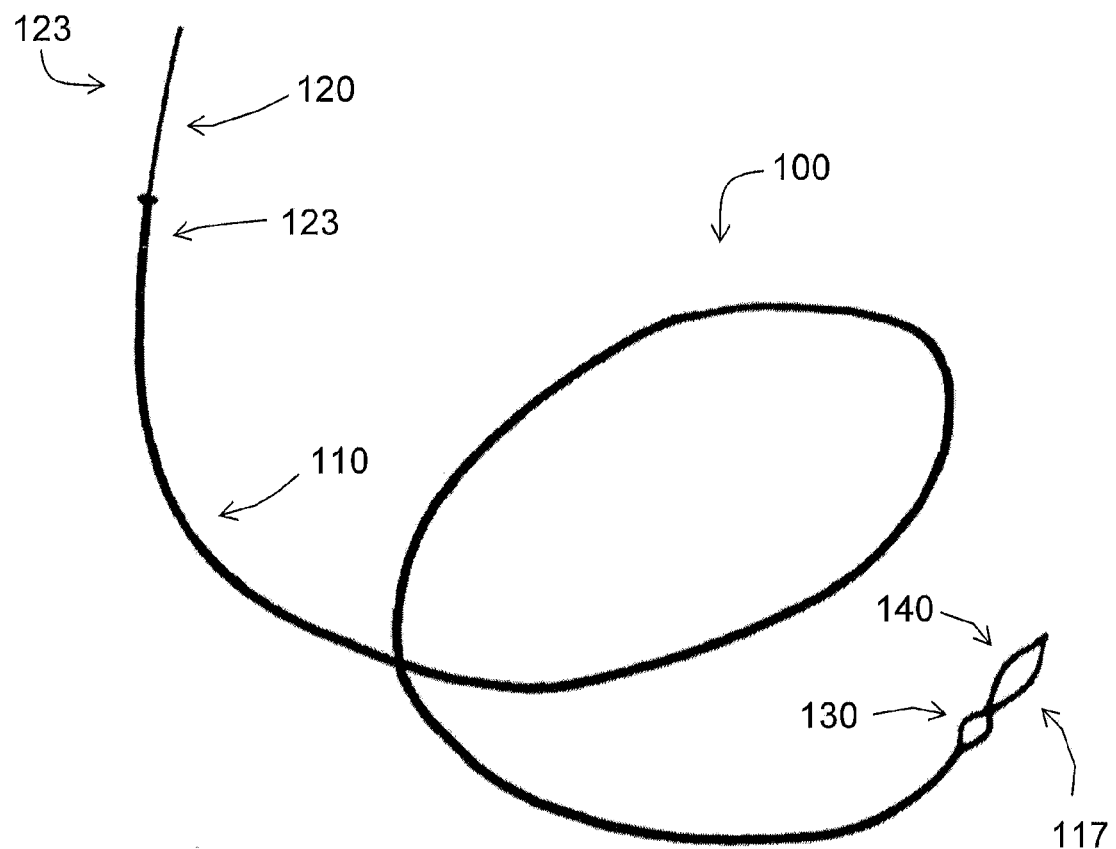
FIG. 1 shows an embodiment of a catheter for measuring the size of a gastric pouch.
Figure 2:
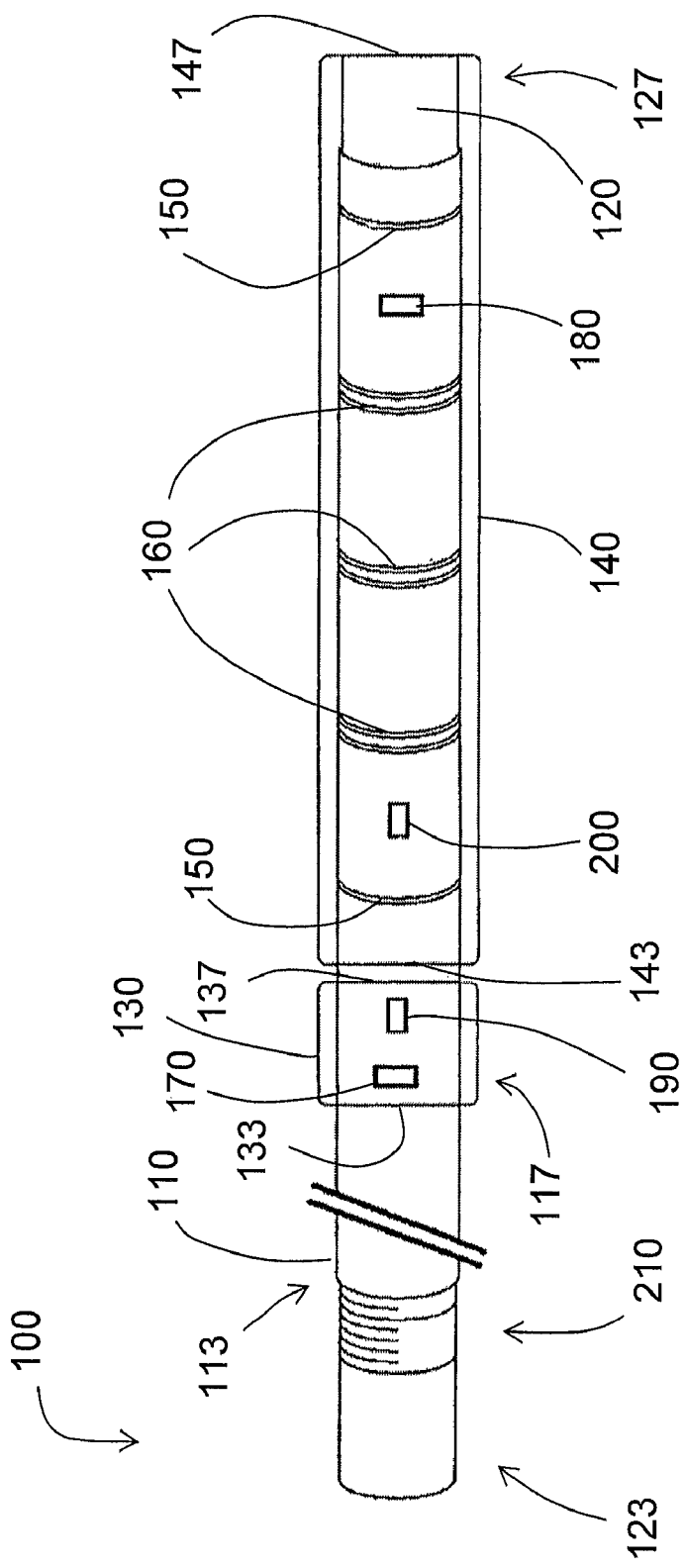
FIG. 2 shows a close-up view of the embodiment of FIG. 1.

FIGS. 1 and 2 show an exemplary embodiment of a catheter for measuring the size of a gastric pouch. Catheter 100 comprises an outer elongate tube 110, having a proximal end 113 and a distal end 117, and an inner elongate tube 120, having a proximal end 123 and a distal end 127. Inner elongate tube 120 is disposed within outer elongate tube 110 such that inner elongate tube 120 is capable of sliding within, and therefore in relation to, outer elongate tube 110. Outer elongate tube 110 is hollow so that inner elongate tube 120 may fit within outer elongate tube 110. Inner elongate tube 120 is shown in FIGS. 1 and 2 as a solid shaft—without a hollow center—but other catheter embodiments may include an inner elongate tube that is hollow.

Catheter 100 includes a proximal balloon 130 that surrounds a portion of outer elongate tube 110 near the distal end 117 of outer elongate tube 110. As shown in the exemplary embodiment in FIG. 2, proximal balloon 130 has a first end 133 and a second end 137, each of which is attached to outer elongate tube 110. As is discussed in more detail below, proximal balloon 130 is used to identify and locate the lower esophageal sphincter at the gastroesophageal junction. Proximal balloon 130 is sized for locating the lower esophageal sphincter, but other embodiments may include proximal balloons that vary slightly in length, based on the circumstances. A person of ordinary skill in the art will understand, based upon this disclosure, the proper length of the proximal balloon to be used.

Proximal balloon 130 is made from commonly known materials in the art, such as polyurethane, silicone, or any other suitable material. It is made from enough material that it can expand circumferentially so that, as is explained in more detail below, any increase in intra-balloon pressure during expansion is due to the body wall surrounding the balloon rather than the tension of the balloon itself.

Catheter 100 also includes a distal balloon 140 that surrounds a portion of outer elongate tube 110 that is distal to proximal balloon 130. Distal balloon 140 has a first end 143 that is attached to outer elongate tube 110 and a second end 147 that is attached to inner elongate tube 120. Consequently, distal balloon 140 is axially adjustable so that it can be elongated or shortened, as desired, by sliding inner elongate tube 120 within outer inner elongate tube 110. Distal balloon 140 is elongated by sliding inner elongate tube 120 so that distal end 127 of inner elongate tube 120 extends past distal end 117 of outer elongate tube 110. Distal balloon 140 increases in length as distal end 127 of inner elongate tube 120 extends further past distal end 117 of outer elongate tube 110. Distal balloon 140 then decreases in length as distal end 127 of inner elongate tube 120 is moved closer to distal end 117 of outer elongate tube 110 until distal end 127 of inner elongate tube 120 is aligned with distal end 117 of outer elongate tube 110.

Distal balloon 140 is generally about three centimeters in length initially and may be axially extended to approximately four or five centimeters in length. It is made from commonly known non-conductive materials in the art, such as polyurethane, silicone, or any other suitable non-conductive material, and is made from sufficient material that it can expand circumferentially as well as axially. Indeed, distal balloon 140 may be made from enough excess material that, as is explained in more detail below, any increase in intra-balloon pressure during balloon expansion is due to the body wall surrounding the balloon rather than the balloon itself.

Attached to the portion of outer elongate tube 110 that is surrounded by distal balloon 140 are two excitation electrodes 150. Specifically, each of excitation electrodes 150 has a proximal end that is capable of attachment to a power source (not shown), such as a battery, and a distal end that is located on outer elongate tube 110 distally to first end 143 of distal balloon 140.

Also attached to outer elongate tube 110, between excitation electrodes 150, are three detection electrodes 160, spaced approximately one centimeter apart. Each of detection electrodes 160 has a proximal end that is capable of attachment to a processor or processing system (not shown), such as a personal computer, and a distal end that is located on outer elongate tube 110 between excitation electrodes 150. Excitation electrodes 150 are configured to emit a measured electrical charge into the inside of distal balloon 140, while detection electrodes 160 detect the amount of the charge that travels through a fluid within distal balloon 140. As explained in more detail below, a processing system calculates the change in electrical charge to determine the conductance through the inside of distal balloon 140 at any given location in the balloon. Although catheter 100 is shown as having three detection electrodes 160, other catheter embodiments may have as few as one or two detection electrodes, or as many as four or more detection electrodes. In addition, although detection electrodes 160 are positioned approximately one centimeter apart, the distance between the detection electrodes on other catheter embodiments may vary.

Catheter 100 also comprises first pressure transducer 170 and second pressure transducer 180. First pressure transducer 170 is attached to the portion of outer elongate tube 110 that is surrounded by proximal balloon 130. It is therefore capable of detecting the pressure, including changes in pressure, within proximal balloon 130. Second pressure transducer 180 is attached to the portion of elongate tube 120 that is surrounded by distal balloon 140. It is therefore capable of detecting the pressure, including changes in pressure, within distal balloon 140.

Proximal balloon 130 and distal balloon 140 are extended circumferentially by inflation with fluid. Catheter 100 further includes a first fluid passageway 190 that extends from a fluid inlet or source (not shown) to the portion of outer elongate tube 110 surrounded by proximal balloon 130. First fluid passageway 190 is designed for injecting fluid, which may comprise saline solution or some other suitable fluid, into proximal balloon 130. Proximal balloon 130 distends as it fills with fluid, until proximal balloon 130 expands to fill the space within the gastric pouch or other cavity.

Likewise, catheter 100 also includes a second fluid passageway 200 that extends from a fluid inlet or source (not shown) to the portion of outer elongate tube 110 surrounded by distal balloon 140. Second fluid passageway 200 is designed for injecting fluid, which may comprise saline solution or some other suitable conductive fluid, into distal balloon 140. Distal balloon 140 distends as it fills with fluid, until distal balloon 140 expands to fill the space within the gastric pouch or other cavity in which it is disposed.

Inner elongate tube 120 includes several gradations 210 at or near proximal end 123 of inner elongate tube 120. Gradations 210 are markings positioned on inner elongate tube 120 two millimeters apart, but the gradations of other embodiments may be spaced apart any suitable predetermined distance (e.g., one millimeter, three millimeters, four millimeters, five millimeters, or one-sixteenth of an inch). The gradations help the practitioner determine the axial length of the distal balloon when the distal end of the catheter has been inserted into the body, and they therefore help the practitioner determine the length of the gastric pouch. Indeed, the practitioner may adjust the length of the distal balloon using the gradations for accuracy.

In the embodiment shown in FIG. 2, inner elongate tube 120 fits snugly within outer elongate tube 110. Although the practitioner can easily slide inner elongate tube 120 back and forth within outer elongate tube 110, inner elongate tube 120 does not inadvertently slide within outer elongate tube 110 because friction holds the two tubes together. The arrangement is also leak-proof such that the fluid remains in the lumen of the balloon.

Figure 3:
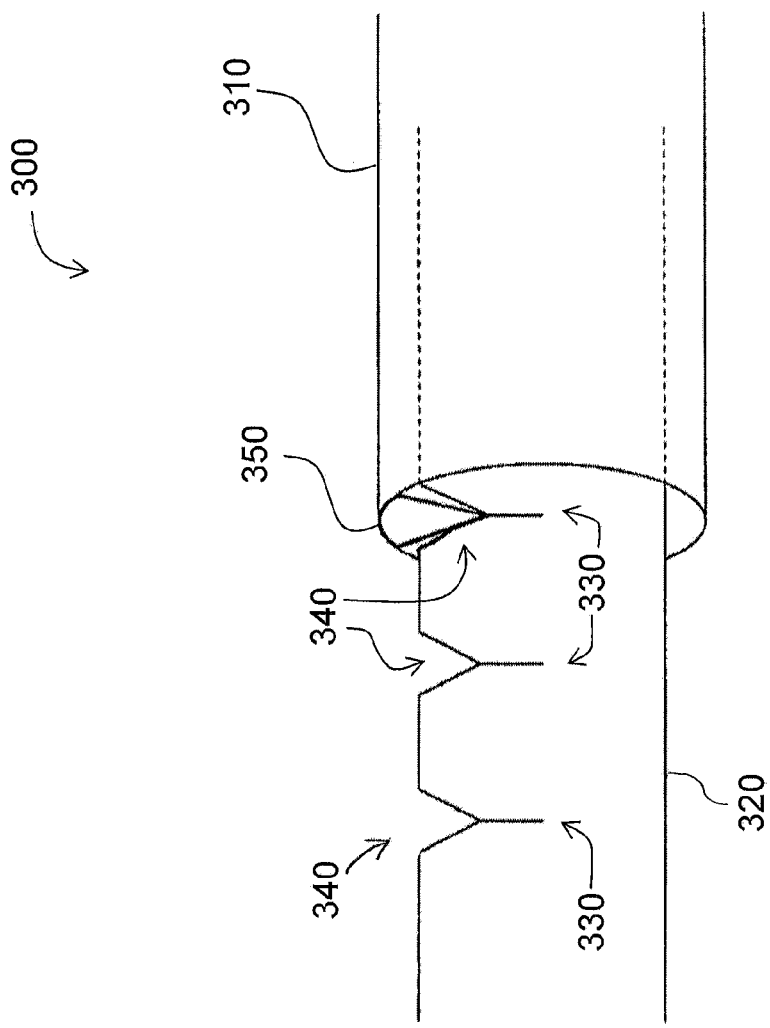
FIG. 3 shows a close-up view of another embodiment of a catheter for measuring the size of a gastric pouch.

In some catheter embodiments, however, the inner elongate tube and outer elongate tube are engaged and held stationary to one another not merely due to friction, but also by a latch and notch engagement. As shown in FIG. 3, catheter 300 includes outer elongate tube 310 and inner elongate tube 320, which includes gradations 330. Gradations 330 comprise notches 340 on inner elongate tube 320, and outer elongate tube 310 has a latch 350 at the proximal end of outer elongate tube 310 that is configured to engage each of notches 340 such that inner elongate tube 320 and outer elongate tube 310 are reversibly fastened to each other. Specifically, latch 350 is somewhat flexible to bend when latch 350 is not aligned with one of notches 340; however, latch 350 extends to engage one of notches 340 when a notch is aligned with latch 350. This engagement holds inner elongate tube 320 in place (with respect to outer elongate tube 310) until the practitioner purposefully slides inner elongate tube 320 by exerting sufficient force on inner elongate tube 320 to cause latch 350 to bend and release its engagement with one of notches 340. Thus, the engagement of the latch and notch is released, allowing retraction or further extension of the distal balloon.

Although catheter 300 is shown with a notch and latch engagement system, any other means for holding the inner and outer elongate tubes in their relative positions may be used. Indeed, as discussed above, mere friction may be sufficient to hold the two tubes in place with respect to each other.

Figure 4B:
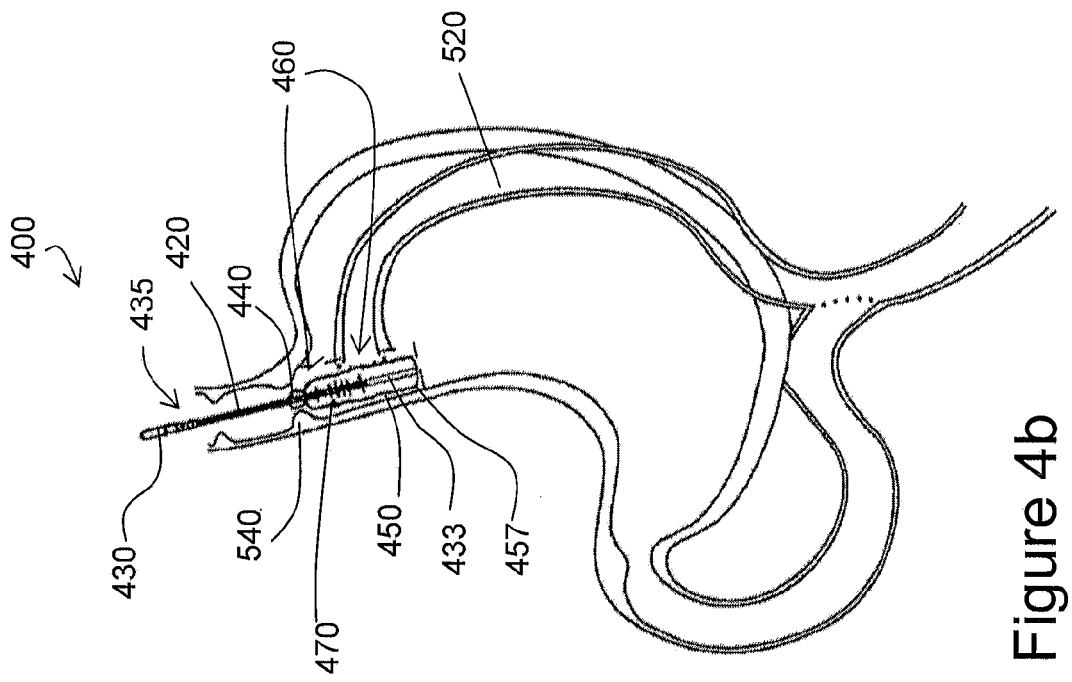
FIG. 4b shows the embodiment of FIG. 4a with its distal balloon axially extended.
Figure 4A:
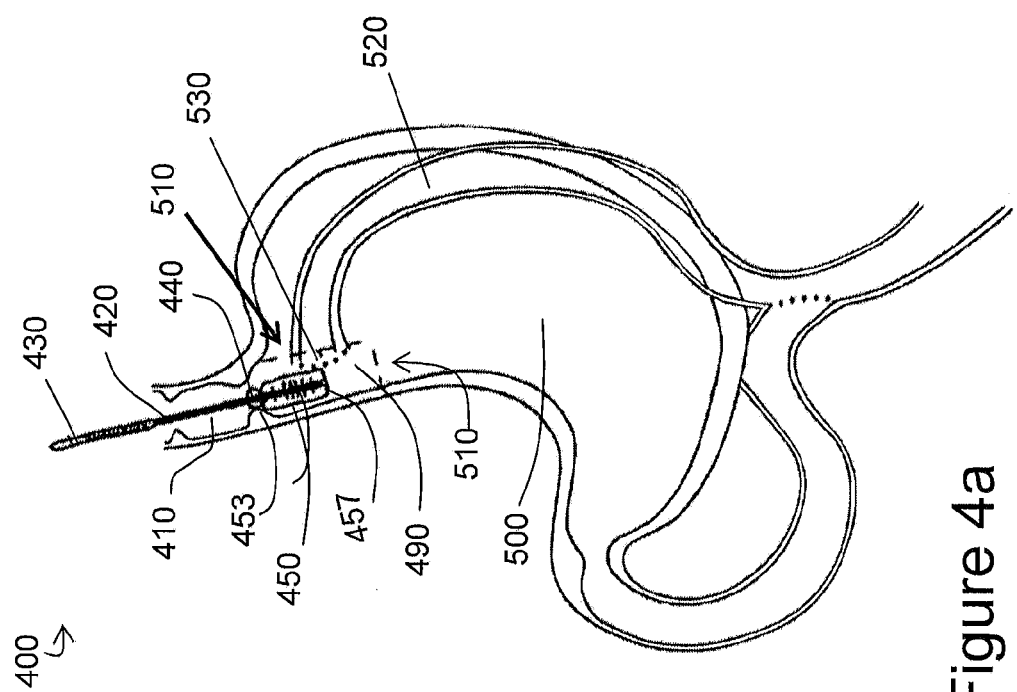
FIG. 4a shows another embodiment of a catheter within a gastric pouch created by a Roux-en-Y Gastric Bypass procedure.

Referring now to FIGS. 4a and 4b, catheter 400 is shown being used to measure the size of a patient's gastric pouch after the patient has undergone a Roux-en-Y bypass procedure. Catheter 400 comprises an outer elongate tube 420 and an inner elongate tube 430 disposed within outer elongate tube 420. Attached to outer elongate tube 420 is proximal balloon 440 and the first end 453 of distal balloon 450. The second end 457 of distal balloon 450 is attached to distal end 433 of inner elongate tube 430. Therefore, as explained with respect to distal balloon 140 of catheter 100, the length of distal balloon 450 may be elongated or shortened by sliding inner elongate tube 430 in relation to outer elongate tube 420.

Catheter 400 further comprises two excitation electrodes 460 positioned on outer elongate tube 420 and four detection electrodes 470 positioned on outer elongate tube 420 between excitation electrodes 460. All of excitation electrodes 460 and detection electrodes 470 are positioned on outer elongate tube 420 within distal balloon 450. Also attached to outer elongate tube 420 within distal balloon 450 is a first pressure transducer (not shown). Second pressure transducer (not shown) is attached to outer elongate tube 420 within proximal balloon 440.

Under general anesthesia, sterilized catheter 400 is introduced into esophagus 410 and advanced to gastric pouch 490, which is formed by closure of the stomach 500 using staples 510. As shown in FIGS. 4a and 4b, the lower portion of the patient's jejunum 520 is attached to gastric pouch 490, thereby forming anastomoses 530.

To properly locate distal balloon 450 within gastric pouch 490, the practitioner locates gastroesophageal junction 540 using proximal balloon 440. Positioning proximal balloon 440 within gastroesophageal junction 540 properly positions distal balloon 450 within gastric pouch 490 for measuring the size of gastric pouch 490.

Gastroesophageal junction 540 may be located (through a process commonly called manometry) by positioning proximal balloon 440 at a location at or near gastroesophageal junction 540, then injecting fluid into proximal balloon 440 to extend proximal balloon 440 circumferentially. As proximal balloon 440 expands circumferentially, the practitioner will monitor the pressure in proximal balloon 440 using readings from the second pressure transducer. Based on these readings, the practitioner can effectively locate gastroesophageal junction 540 because the lower esophageal sphincter at the junction—being a muscle—causes a more rapid rise in pressure upon balloon inflation than does the esophageal tissue or stomach tissue surrounding the junction 540. Therefore, through a trial-and-error process of inflating the proximal balloon and reading the consequent intra-balloon pressures, the practitioner can effectively locate the gastroesophageal junction, thereby locating the gastric pouch. Distal balloon 450 remains deflated during positioning of catheter 400.

Once catheter 400 is in proper position, and therefore distal balloon 450 is located within gastric pouch 490, as shown in FIG. 4a, distal balloon 450 is adjusted axially to a desired balloon length, usually based on the size of gastric pouch 490. For example, as shown in FIG. 4b, distal balloon 450 has been extended axially to the wall of gastric pouch 490 by the practitioner sliding inner elongate tube 430 within outer elongate tube 420. In other words, inner elongate tube 430 has been pushed forward so that distal end 433 of inner elongate tube 430 extends past the distal end of outer elongate tube 420, thereby elongating distal balloon 450.

The practitioner may adjust distal balloon 450 axially to a desired balloon length by sliding inner elongate tube 430 within outer elongate tube 420 until one of gradations 435 on inner elongate tube 430 is aligned with the proximal end of outer elongate tube 420. Alternatively, with respect to catheter embodiments having a notch and latch mechanism, such as catheter 100 discussed above, the practitioner may adjust the distal balloon axially to a desired balloon length by sliding the inner elongate tube within the outer elongate tube until one of the gradations on the inner elongate tube is engaged by a latch on the proximal end of the outer elongate tube, thereby reversibly fastening the inner elongate tube and the outer elongate tube.

In some cases, the distal balloon may have to be shortened for proper measuring of gastric pouch size. In such cases, the practitioner may shorten the distal balloon axially by sliding the inner elongate tube within the outer elongate tube. Specifically, the practitioner could pull back on the inner elongate tube so that the distal end of the inner elongate tube is drawn toward the distal end of the outer elongate tube, thereby shortening the distal balloon. The practitioner may adjust the distal balloon axially to a desired balloon length by sliding the inner elongate tube within the outer elongate tube until one of the gradations on the inner elongate tube is aligned with the proximal end of the outer elongate tube. Alternatively, with respect to catheter embodiments having a notch and latch mechanism, such as catheter 100 discussed above, the practitioner may adjust the distal balloon axially to a desired balloon length by sliding the inner elongate tube within the outer elongate tube until one of the gradations on the inner elongate tube is engaged by a latch on the proximal end of the outer elongate tube, thereby reversibly fastening the inner elongate tube and the outer elongate tube.

Referring again to FIGS. 4a and 4b, after the size of distal balloon 450 is adjusted axially, fluid is injected into distal balloon 450 to extend distal balloon 450 circumferentially. As explained with respect to proximal balloon 440 above, as fluid fills distal balloon 450, the balloon will distend circumferentially to fill the space within gastric pouch 490. As explained below, saline solution may be used as the fluid injected into distal balloon 450. Although other conductive fluids may be used with the catheter, potentially toxic fluids should be avoided.

Using catheter 400, the practitioner can determine a number of size variables of gastric pouch 490 (e.g., approximate length, cross-sectional area, volume). Tension and compliances may also be determined. First, the practitioner can determine the approximate length of gastric pouch 490 by referencing gradations 435 on inner elongate tube 430. For example, if the catheter gradations are set one millimeter apart, the practitioner can determine how many millimeters the distal balloon has been extended beyond its initial length.

Second, the practitioner can determine an approximate cross-sectional area of gastric pouch 490, often at a number of different locations within the pouch. To determine cross-sectional area, electrical impedance (or conductance) is measured within distal balloon 450 using excitation electrodes 460 and detection electrodes 470. Such measurements are described in detail in Kassab et al., System and Method for Measuring Cross Sectional Areas and Pressure Gradients in Luminal Organs (Publ. No. US 2004/0230131 A1), which is incorporated herein by reference. In short, the cross-sectional area is estimated from measurements of the electrical impedance inside the distal balloon using two or more electrodes according to Ohm's law. The voltage difference between the detection electrodes depends on the magnitude of the current (I) multiplied by the distance (L) between the detection electrodes and divided by the conductivity (C) of the fluid and the cross-sectional area (CSA) of the balloon. Since the current (I), the distance (L), and the conductivity (C) normally can be regarded as calibration constants, an inverse relationship exists between the voltage difference and the cross-sectional area as shown:

$$CSA = \frac{GL}{C}$$

where G is conductance expressed as the ratio of current to voltage (I/ΔV). In other words, the voltage drop along each detection electrode is measured and converted into a cross-sectional area via a calibration.

The cross-sectional area determination is relatively accurate because a non-conductive material is used for the distal balloon, inhibiting loss of electric current from the fluid within the balloon. When the distal balloon is distended to fill the gastric pouch in which it is placed (and therefore match the shape of the gastric pouch), the cross-sectional area of the distal balloon matches the cross-sectional area of the gastric pouch itself. Thus, determining a cross-sectional area of a portion of the distal balloon leads to a determination of the cross-sectional area of a portion of the gastric pouch.

Depending on the number of detection electrodes on the catheter being used, the practitioner can determine the cross-sectional area of the gastric pouch at more than one location, thereby increasing the accuracy of certain size determinations. For example, as shown in FIGS. 4a and 4b, catheter 400 includes four detection electrodes 470. Thus, because the cross-sectional area may be determined at each of the detection electrodes, the practitioner using catheter 400 can determine the cross-sectional area of the gastric pouch at four locations without moving the catheter. As is discussed below, using four different cross-sectional areas generally provides for a more accurate gastric pouch volume determination as compared to the use of fewer cross-sectional areas.

Third, the practitioner can determine the approximate volume of gastric pouch 490. Pouch volume can be determined by multiplying the length of gastric pouch 490 by the average cross-sectional area of gastric pouch 490. Consequently, the volume determination will generally be more accurate if the number of cross-sectional area determinations are increased. The following formula is used:

$$V = L * \frac{1}{N} \sum_{i=1}^{N} CSA_i$$

where V is the volume of the pouch, L is the length of the pouch, N is the number of detection electrodes (and therefore the number of different cross-sectional area determinations), and CSA is the cross-sectional area. If the cross-sectional area varies significantly due to the non-uniform geometry of the pouch such that the mean cross-sectional area is not accurate, the following formula may be used:

$$V = \sum_{i=1}^{N} L_i CSA_i$$

Finally, each of these size variables of gastric pouch 490 can be determined when gastric pouch 490 is in different states. Two of the most important states for clinical applications are when gastric pouch 490 is relatively empty, which shows the pouch's resting size, and when gastric pouch 490 is full, which shows the pouch's maximum capacity. The practitioner can determine the relative state of gastric pouch 490 using the pressure within distal balloon 450, as determined by the first pressure transducer. Thus, determining a size variable of the gastric pouch often comprises determining a pressure inside the distal balloon.

To determine a size variable of gastric pouch 490 at its resting size, distal balloon 450 should be extended to fill gastric pouch 490, but should not be extended so much that the balloon itself expands the walls of the gastric pouch. As the practitioner injects fluid into distal balloon 450, the practitioner references the intra-balloon pressure determined by the first pressure transducer. Gastric pouch 490 is considered at its resting size just prior to an increase in intra-balloon pressure during balloon expansion.

To determine a size variable of gastric pouch 490 at its maximum capacity size, distal balloon 450 is extended beyond the pouch's resting size. Based on determination of the intra-balloon pressure, the practitioner can determine when distal balloon 450 has enlarged the gastric pouch 490 to its maximum capacity. As distal balloon 450 is filled past the pouch resting size, the walls of gastric pouch 490 exert force on distal balloon 450, thereby causing a relatively steadily increasing intra-balloon pressure. The pouch is considered to be at its maximum capacity when the pressure no longer steadily increases, but instead plateaus.

Figure 5:
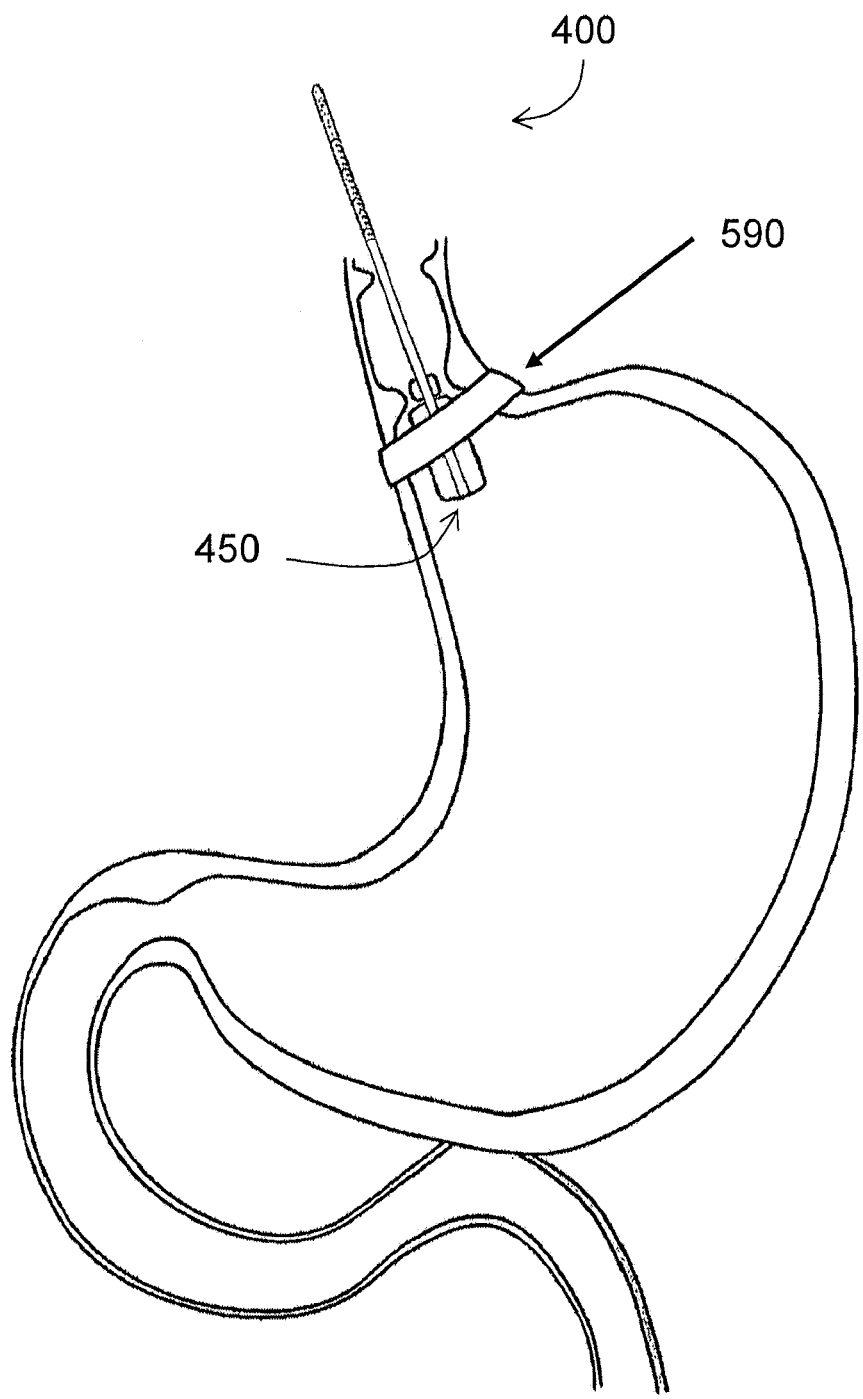
FIG. 5 shows the embodiment of FIGS. 4a and 4b within a gastric pouch formed by an AGB band.

Referring now to FIG. 5, there is shown catheter 400 being used to size a gastric band 590. Thus, instead of being placed in gastric pouch 490, which was formed by staples 510, as shown in FIG. 4a, FIG. 5 shows distal balloon 450 being placed to size a gastric pouch formed via constriction by gastric band 590.

Figure 6:
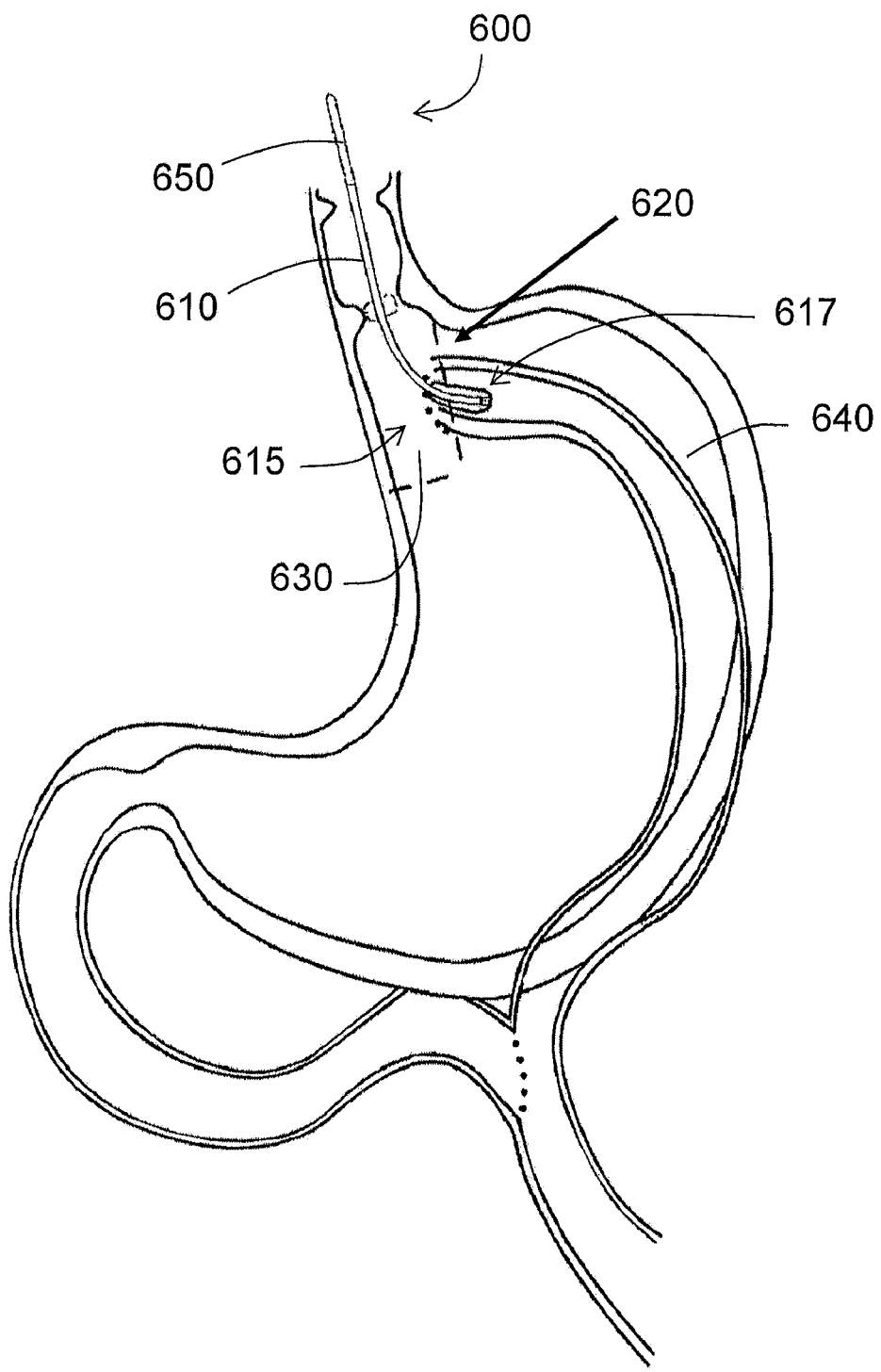
FIG. 6 shows another embodiment of a catheter used to size the gastric-intestinal anastomosis.

Referring now to FIG. 6, catheter 600 is similar to catheter 400, discussed above. However, catheter 600 includes outer elongate tube 610 that comprises flexible portion 615 near distal end 617 of outer elongate tube 610. As shown, flexible portion 615 is capable of being bent into a curve so that the practitioner can measure the size of anastomoses 620 between gastric pouch 630 and lower portion of jejunum 640. Thus, embodiments disclosed herein may be used to measure the size of gastric pouches, as well as anastomoses and other gastric lumens. Indeed, as used herein, the term "gastric pouch" may refer to a gastric pouch formed by sutures, staples, or a band, a gastric/intestinal anastomoses, or any other gastric lumen suitable for sizing in accordance with the embodiments disclosed herein.

Catheter 600 further comprises an inner elongate tube 650. Inner elongate tube 650 is flexible so that it is capable of sliding within flexible portion 615 when flexible portion 615 is bent into a curve.

Although catheter 600 includes outer elongate tube 610 having flexible portion 615, other embodiments of catheters similar to catheter 600 have outer elongate tubes that, instead of having a flexible portion, may have a curved portion similar to flexible portion 615 when flexible portion 615 is bent into a curve. In those embodiments, the inner elongate tube is flexible so that the inner elongate tube is capable of sliding within the curved portion of the outer elongate curve.

Figure 7:
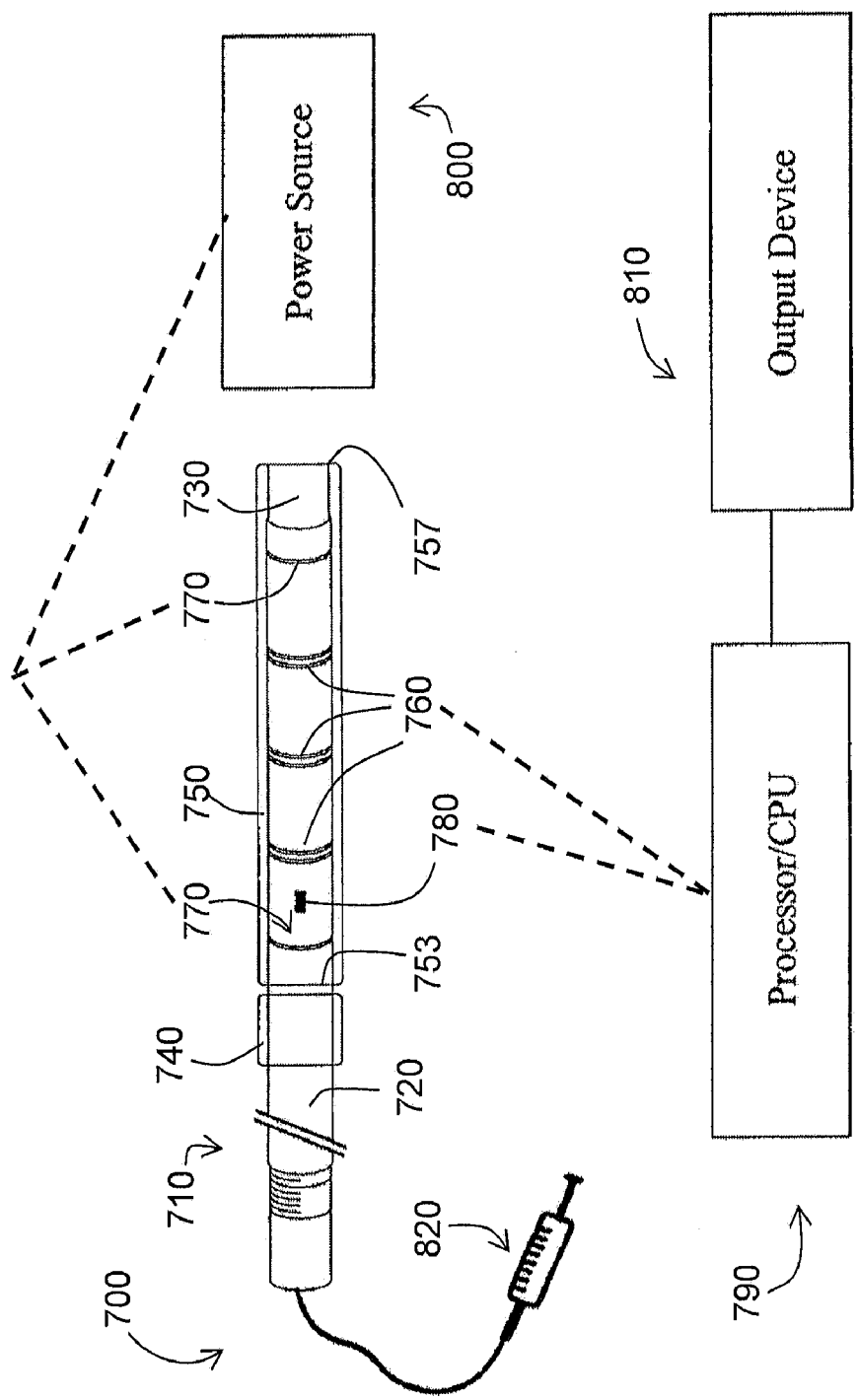
FIG. 7 shows an embodiment of a system for measuring the size of a gastric pouch.

Referring now to FIG. 7, there is shown system 700 for measuring the size of a gastric pouch or other gastric lumen. System 700 comprises catheter 710 comprising an outer elongate tube 720, an inner elongate tube 730 disposed within outer elongate tube 720, a proximal balloon 740 attached to outer elongate tube 720, a distal balloon 750 having a first end 753 attached to outer elongate tube 720 and a second end 757 attached to inner elongate tube 730, three detection electrodes 760 positioned on outer elongate tube 720 between two excitation electrodes 770, and a pressure transducer 780 positioned on outer elongate tube 720.

System 700 further comprises a first processor 790 operatively connected to detection electrodes 760. First processor 790 comprises a computer capable of collecting conductance data (i.e., impedance data) and determining various size variables, in accordance with the present disclosure. System 700 also comprises a power source 800, which is operatively connected to excitation electrodes 770.

First processor 790 is also operatively connected to pressure transducer 780 and is capable of collecting pressure data generated by pressure transducer 780. First processor 790 displays pressure data, conductance/impedance data, and various size variables via a graphical display screen or other output device 810. Alternatively, in some embodiments, the first processor is not operatively connected to the pressure transducer. Instead, those systems comprise a second processor that is operatively connected to the pressure transducer such that the second processor is capable of collecting pressure data.

System 700 further comprises a fluid source 820 operatively connected to the catheter such that a fluid from fluid source 820 can be injected into proximal balloon 740 or into distal balloon 750. As shown in FIG. 7, fluid source 820 comprises a syringe or pump.

The various embodiments of devices, systems, and methods that are disclosed herein may be used to determine various size-variables with respect to existing pouches or for use in creating new pouches. The embodiments should enable practitioners to standardize new procedures and to correlate pouch size with other clinical parameters to determine clinical outcomes and prognoses.

While various embodiments of devices, systems, and methods for sizing of gastric pouches have been described in considerable detail herein, the embodiments are merely offered by way of non-limiting examples of the invention described herein. Many variations and modifications of the embodiments described herein will be apparent to one of ordinary skill in the art in light of this disclosure. It will therefore be understood by those skilled in the art that various changes and modifications may be made, and equivalents may be substituted for elements thereof, without departing from the scope of the invention. Indeed, this disclosure is not intended to be exhaustive or to limit the scope of the invention. The scope of the invention is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present invention.

It is therefore intended that the invention will include, and this description and the appended claims will encompass, all modifications and changes apparent to those of ordinary skill in the art based on this disclosure.

I claim:

1. A catheter for measuring a size of a gastric pouch, comprising:

an outer elongate tube having a proximal end and a distal end;

an inner elongate tube having a proximal end and a distal end, the inner elongate tube positioned at least partially within the outer elongate tube such that the inner elongate tube is capable of sliding within the outer elongate tube;

a proximal balloon surrounding at least a portion of the outer elongate tube near the distal end of the outer elongate tube, the proximal balloon having a first end attached to the outer elongate tube and a second end attached to the outer elongate tube;

a distal balloon surrounding a portion of the outer elongate tube distal to the proximal balloon, the distal balloon having a first end attached to the outer elongate tube and a second end attached to the inner elongate tube;

at least two excitation electrodes attached to the portion of the outer elongate tube surrounded by the distal balloon, the at least two excitation electrodes capable of attachment to a power source;

at least two detection electrodes attached to the outer elongate tube positioned relative to the at least two excitation electrodes, the at least two detection electrodes capable of attachment to a processor;

a first pressure transducer attached to the portion of the outer elongate tube surrounded by the proximal balloon; and a second pressure transducer attached to the portion of the outer elongate tube surrounded by the distal balloon.

2. The catheter of claim 1, wherein the at least two detection electrodes comprise three or more detection electrodes.

3. The catheter of claim 1, further comprising:
a first fluid passageway for injecting fluid into the proximal balloon; and
a second fluid passageway for injecting fluid into the distal balloon.

4. The catheter of claim 1, wherein the inner elongate tube comprises at least one gradation at or near the proximal end of the inner elongate tube.

5. The catheter of claim 4, wherein the at least one gradation comprises at least two gradations positioned on the inner elongate tube a predetermined distance apart.

6. The catheter of claim 5, wherein the at least two gradations comprise notches on the inner elongate tube, and wherein the outer elongate tube comprises a latch at or near the proximal end of the outer elongate tube, the latch configured to engage one or more of the notches such that the inner elongate tube and the outer elongate tube are reversibly fastened.

7. The catheter of claim 6, wherein the outer elongate tube comprises a flexible portion near the distal end of the outer elongate tube, the flexible portion capable of being bent into a curve, and wherein the inner elongate tube is flexible such that the inner elongate tube is capable of sliding within the flexible portion of the outer elongate tube when the flexible portion is bent into a curve.

8. The catheter of claim 6, wherein the outer elongate tube comprises a curved portion near the distal end of the outer elongate tube, and wherein the inner elongate tube is flexible such that the inner elongate tube is capable of sliding within the curved portion of the outer elongate tube.

9. A system for measuring a size of a gastric pouch, comprising:
a catheter comprising:
an outer elongate tube, and an inner elongate tube positioned at least partially within the outer elongate tube;
a proximal balloon attached to the outer elongate tube;
a distal balloon having a first end attached to the outer elongate tube and a second end attached to the inner elongate tube;
at least two detection electrodes positioned on the outer elongate tube positioned relative to at least two excitation electrodes; and
a pressure transducer positioned on the outer elongate tube;
a first processor operatively connected to at least two of the at least two detection electrodes, the first processor capable of collecting conductance data and determining at least one size variable; and
a power source operatively connected to at least two of the at least two excitation electrodes, the power source capable of providing current to the at least two excitation electrodes.

10. The system of claim 9, wherein the catheter further comprises a first fluid passageway for injecting fluid into the proximal balloon and a second fluid passageway for injecting fluid into the distal balloon.

11. The system of claim 9, wherein the first processor is operatively connected to the pressure transducer, the first processor being capable of collecting pressure data.

12. The system of claim 9, further comprising a second processor operatively connected to the pressure transducer, the second processor being capable of collecting pressure data.

13. The system of claim 9, wherein the at least one size variable is selected from a group consisting of an approximate cross-sectional area of the gastric pouch and an approximate volume of the gastric pouch.

14. The system of claim 9, further comprising a fluid source operatively connected to the catheter, such that a fluid from the fluid source can be injected into the proximal balloon or the distal balloon.

15. The system of claim 14, wherein the inner elongate tube comprises at least one gradation near the proximal end of the inner elongate tube.

16. The system of claim 14, wherein the fluid source comprises a syringe.

17. The system of claim 11, further comprising a graphical display screen coupled to the first processor, the graphical display screen operable to displaying pressure data or at least one size variable.

* * * * *